(12) United States Patent
Rousseau et al.

(10) Patent No.: US 6,712,859 B2
(45) Date of Patent: Mar. 30, 2004

(54) HERNIA REPAIR PROSTHESIS AND METHODS FOR MAKING SAME

(75) Inventors: Robert A. Rousseau, Ottsville, PA (US); David Lindh, Somersworth, NH (US)

(73) Assignee: Ethicon, Inc., Somerville, NJ (US)

( * ) Notice: Subject to any disclaimer, the term of this patent is extended or adjusted under 35 U.S.C. 154(b) by 28 days.

(21) Appl. No.: 09/894,713

(22) Filed: Jun. 28, 2001

(65) Prior Publication Data

US 2003/0004579 A1 Jan. 2, 2003

(51) Int. Cl.$^7$ .............................. A61F 2/04; A61B 17/08
(52) U.S. Cl. ..................................... 623/23.64; 606/151
(58) Field of Search ........................... 623/23.64, 23.65, 623/23.7–23.72, 23.75; 606/151

(56) References Cited

U.S. PATENT DOCUMENTS

| | | |
|---|---|---|
| 2,671,444 A | 3/1954 | Pease, Jr. |
| 3,054,406 A | 9/1962 | Usher |
| 4,347,847 A | 9/1982 | Usher |
| 4,452,245 A | 6/1984 | Usher |
| 4,561,434 A | 12/1985 | Taylor |
| 4,744,364 A | 5/1988 | Kensey |
| 4,769,038 A | 9/1988 | Bendavid et al. |
| 4,796,603 A | 1/1989 | Dahlke et al. |
| 4,852,568 A | 8/1989 | Kensey |
| 4,854,316 A | 8/1989 | Davis |
| 5,021,059 A | 6/1991 | Kensey et al. |
| 5,059,205 A | 10/1991 | El-Nounou et al. |
| 5,061,274 A | 10/1991 | Kensey |
| 5,108,420 A | 4/1992 | Marks |
| 5,108,430 A | 4/1992 | Ravo |
| 5,116,357 A | 5/1992 | Eberbach |
| 5,122,155 A | 6/1992 | Eberbach |
| 5,141,515 A | 8/1992 | Eberbach |

(List continued on next page.)

FOREIGN PATENT DOCUMENTS

| | | |
|---|---|---|
| EP | 0544485 | 6/1993 |
| EP | 0573273 | 12/1993 |
| EP | 0655222 | 5/1995 |
| EP | 0888756 | 1/1999 |
| EP | 0898944 | 3/1999 |
| EP | 1145693 | 10/2001 |
| WO | 9213500 | 8/1992 |
| WO | 9507666 | 3/1995 |
| WO | 9530374 | 11/1995 |
| WO | 9735533 | 10/1997 |

*Primary Examiner*—Nicholas D. Lucchesi
*Assistant Examiner*—Fenn C Mathew (57) ABSTRACT

A hernia repair prosthesis with an occlusive member for inserting into and/or backing the herniated tissue. The occlusive member is convertible from a first configuration with a first axial length and first major radial extent to a second configuration with a second axial length and a second major radial extent. The second axial length is less than the first axial length and the second major radial extent is larger than the first major radial extent. The occlusive member has a pair of subsections, each having an apex, lands and pleats and each flaring outwardly therefrom towards a terminal end. The apexes are disposed at opposite ends of the occlusive member with the terminal ends overlapping. The pair of subsections are conjoined proximate the overlapping terminal ends. The terminal end of one or both of the subsections may be in the form of a conic flange mimicking the lands and pleats of the other subsection providing automatic alignment and nesting to aid in the attachment of the two subsections. In accordance with methods for forming the subsections, a surgical fabric is thermoset on a male die and may be stretched or heat shrunk to aid in conforming the surgical fabric to the contours of the male die. The subsections may be joined by ultrasound.

15 Claims, 4 Drawing Sheets

U.S. PATENT DOCUMENTS

| | | |
|---|---|---|
| 5,147,374 A | 9/1992 | Fernandez |
| 5,147,384 A | 9/1992 | La Rocca |
| 5,176,692 A | 1/1993 | Wilk et al. |
| 5,192,302 A | 3/1993 | Kensey et al. |
| 5,246,455 A | 9/1993 | Shikani |
| 5,254,133 A | 10/1993 | Seid |
| 5,258,000 A | 11/1993 | Gianturco |
| 5,290,217 A | 3/1994 | Campos |
| 5,304,187 A | 4/1994 | Green et al. |
| 5,316,543 A | 5/1994 | Eberbach |
| 5,334,217 A | 8/1994 | Das |
| 5,356,432 A * | 10/1994 | Rutkow et al. ............... 623/11 |
| 5,368,602 A | 11/1994 | de la Torre |
| 5,370,650 A | 12/1994 | Tovey et al. |
| 5,383,477 A | 1/1995 | DeMatteis |
| 5,397,331 A | 3/1995 | Himpens et al. |
| 5,425,740 A | 6/1995 | Hutchinson, Jr. |
| 5,456,720 A | 10/1995 | Schultz et al. |
| 5,545,178 A | 8/1996 | Kensey et al. |
| 5,578,045 A | 11/1996 | Das |
| 5,593,441 A | 1/1997 | Lichtenstein et al. |
| 5,634,931 A | 6/1997 | Kugel |
| 5,634,944 A | 6/1997 | Magram |
| 5,686,090 A | 11/1997 | Schilder et al. |
| 5,716,408 A | 2/1998 | Eldridge et al. |
| 5,741,297 A | 4/1998 | Simon |
| 5,743,917 A | 4/1998 | Saxon |
| 5,769,864 A | 6/1998 | Kugel |
| 5,797,960 A | 8/1998 | Stevens et al. |
| 5,824,082 A | 10/1998 | Brown |
| 5,861,003 A | 1/1999 | Latson et al. |
| 5,916,225 A | 6/1999 | Kugel |
| 5,944,738 A * | 8/1999 | Amplatz et al. ............ 606/213 |
| 5,954,767 A | 9/1999 | Pajotin et al. |
| D416,327 S | 11/1999 | Kugel |
| 5,976,174 A | 11/1999 | Ruiz |
| 6,113,623 A | 9/2000 | Sgro |
| 6,113,641 A | 9/2000 | Leroy et al. |
| 6,174,322 B1 | 1/2001 | Schneidt |
| 6,176,863 B1 | 1/2001 | Kugel et al. |
| 6,180,848 B1 | 1/2001 | Flament et al. |
| 6,214,029 B1 | 4/2001 | Thill et al. |
| 6,241,768 B1 | 6/2001 | Agarwal et al. |
| 6,270,515 B1 | 8/2001 | Linden et al. |
| 6,425,924 B1 * | 7/2002 | Rousseau ................. 623/23.64 |

\* cited by examiner

HERNIA REPAIR PROSTHESIS AND METHODS FOR MAKING SAME

FIELD OF THE INVENTION

The present invention relates to an implantable hernia repair prosthesis for reinforcing and repairing damaged tissue or muscle walls and methods for making same.

BACKGROUND OF THE INVENTION

Various prosthetic mesh materials have been proposed to reinforce the abdominal wall and to close abdominal wall defects utilizing different repair prostheses and methods of installation. The methods of executing a surgical repair can be segregated into two main approaches. The repair can be made exclusively from the anterior side (closest to the surgeon) of the defect by dissecting the sac free of the fascia and pressing it back into the pre-peritoneal space and providing permanent closure of the defect. The closure can be provided through the application of space filling prostheses and overlay patches (tension-free techniques) or can be accomplished through the use of sutures (tension techniques).

An example of a tension free anterior repair is to fold a sheet of surgical mesh fabric into a multi-layer cone configuration and then to insert the mesh plug into a hernia defect to occlude the void. Such a multi-layer prosthesis is inherently stiff, may not fully conform to variations in the contour of the defect, and is subject to shrinkage that potentially could lead to recurrent herniation. The stiff, multi-layered mesh plug also may be susceptible to kinking and buckling during placement.

U.S. Pat. No. 5,356,432, discloses an implantable prosthesis that is a conical plug formed of a knitted polypropylene monofilament mesh fabric. Longitudinal pleats are hot molded into the mesh body to enhance the flexibility of the conical implant, ideally allowing the implant to closely match the contour of the herniated opening when compressed within the defect. When the device is installed into a fascial defect, the tip of the conical shaped plug presses into and against the visceral sac, potentially enabling long-term erosion of the peritoneum and underlying viscera. The device, in one embodiment, has filler material incorporated into the interior of the formed mesh cone in an attempt to minimize contraction of the device during healing. As collagen scar tissue grows into the prosthetic material, the cross linking of the maturing collagen fibers causes the scar tissue (and encapsulated plug device) to contract. This contraction of scar tissue within the defect and plug causes the surrounding diseased tissue to be subjected to tension, thus enabling re-occurrence of the hernia along the edge of the conical plug. The use of the device requires the passage of a pre-expanded plug through the hernia defect and relies upon the radial expansion force of the single layer mesh cone and filler leaves to occlude the defect. Additionally, since the plug is secured in position by anchoring to the surrounding diseased tissue, the device may dislodge and migrate within the pre-peritoneal space.

Alternatively, a defect may be repaired through the use of posterior approaches that provide various prosthetic devices in the pre-peritoneal space to prevent the peritoneum from entering the fascial defect. These devices, in some cases, require the use of laparoscopic techniques and, in other cases, require the application of the prosthesis from a remote location under the defect to be repaired. Examples of posterior approaches are disclosed in U.S. Pat. Nos. 5,116,357, 5,254,133 and 5,916,225. However, in many cases, procedures utilizing such devices are complicated, in addition to requiring the use of general anesthesia and costly disposable instrumentation to support the laparoscopic surgery.

Accordingly, the prior art lacks an implantable hernia repair prosthesis for occluding and repairing damaged muscle and tissue wall ruptures, that is adaptable to irregularities in the shape of the defect, is simple to install, does not require the use of general anesthesia during installation and resists radial collapse due to tissue incorporation.

SUMMARY OF THE INVENTION

The limitations of prior art hernia prostheses are overcome by the present invention which includes a hernia repair prosthesis having an occlusive member for aiding in the occlusion of a defect in fascia tissue. The occlusive member is convertible from a first configuration with a first axial length and a first major radial extent to a second configuration with a second axial length and a second major radial extent. The second axial length is less than the first axial length and the second major radial extent is larger than the first major radial extent. The occlusive member has a pair of subsections, each having an apex and each flaring outwardly therefrom towards a terminal end. The apexes are disposed at opposite ends of the occlusive member with the terminal ends overlapping. The pair of subsections are conjoined proximate the overlapping terminal ends.

In accordance with a method for forming the subsections, a surgical fabric is thermoset on a male die and may be stretched or heat shrunk to aid in conforming the surgical fabric to the contours of the male die.

DESCRIPTION OF THE FIGURES

For a better understanding of the present invention, reference is made to the following detailed description of various exemplary embodiments considered in conjunction with the accompanying drawings, in which.

DETAILED DESCRIPTION OF THE INVENTION

The present invention provides implantable prostheses for reinforcing and repairing weakened abdominal walls and methods for making such prostheses. The prostheses are formed of a biologically compatible, flexible and porous medical textile suitable for reinforcing tissue and occluding tissue defects. The implantable prostheses are indicated particularly for the repair of hernias in the abdominal cavity, including inguinal (direct and indirect), femoral, incisional and recurrent, and provide at least a partial posterior repair. The prostheses are able to be inserted easily in a stress-free condition into a fascia defect from an anterior approach and are capable of expanding radially, at least partially into the pre-peritoneal space, to substantially occlude and conform to the fascia wall of a fascia defect. Alternatively, a posterior approach may be used, if the surgeon prefers. The prostheses are suitable for the repair of varying sizes and shapes of hernias and can be anchored to the surrounding healthy tissue to prevent migration, thus extending beyond the edge of the defect on the anterior side of the defect. Other features of the present invention will become apparent from the following detailed description when taken in connection with the accompanying drawings that disclose multiple embodiments of the invention. The drawings are for the purpose of illustration only and are not intended as a definition of the limits of the invention.

The prostheses of the present invention comprise a hollow, radially-expandable member for placement within and occlusion of a fascia defect. By radially-expandable, it is meant that the cross sectional area of the member expands from an initial, non-expanded configuration having an initial cross sectional area, sized such that the member may be placed within a fascia defect in a stress-free condition, to a final, expanded configuration having a final cross sectional area greater than the initial cross sectional area and effective to occlude all of, or at least a substantial portion of, the fascia defect. This member can be manufactured out of biocompatible absorbable or non-absorbable surgical mesh material.

Figure 1:
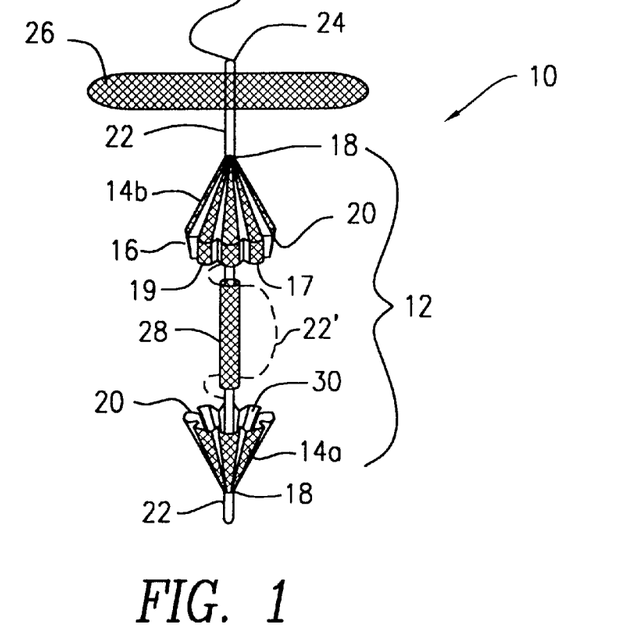
FIG. 1 is a perspective view of a prosthesis according to the present invention prior to assembly of all of its component parts.

An exploded view of a prosthesis of the present invention is illustrated in FIG. 1. Prosthesis 10 comprises radially-expandable member 12, having first and second conical members 14a, 14b. Each conical member 14a, 14b has longitudinal pleats 16 terminating at apex 18 and base 20 of each conical member 14a, 14b, respectively. The number and spacial relationship of longitudinal pleats 16 are effective to enhance the axial rigidity of the prosthesis 10 while being placed within the defect. Preferably, the pleats 16 are thermoformed into the mesh body of each conical member 14a, 14b. Conical member 14b has a flange portion 19 that facilitates the relative alignment and attachment of conical members 14a, 14b, as more fully described below in reference to FIGS. 6 and 7. Looped suture 22, with a non-reversing knot 24, is passed through opposing conical members, 14a, 14b. Overlay sheet 26, e.g., formed from polypropylene surgical mesh, is fixedly attached to apex 18 of one of opposing conical members 14a, 14b through the use of looped suture 22. Overlay sheet 26 is utilized to attach and secure the prosthesis to the surrounding healthy tissue. Optionally, prosthesis 10 may comprise one or more tubular structures 28, e.g., made from polypropylene surgical mesh and contained within cavity 30 within conical members 14a, 14b. Tubular structure 28 provides additional axial rigidity to the prosthesis during handling and insertion of the device into the defect. Tubular structure, as used herein, is meant to include those structures where the cross sectional configuration is tubular in nature. Tubular structure specifically includes cylindrical rolls of materials, e.g. meshes, where the cross section configuration is circular, as well as structures where the cross sectional configuration may be elliptical, triangular, rectangular, etc. The tubular structure 28 also improves the radial expandability of the prosthesis when it is compressed axially and the cylinder collapses, ensuring a solid expansion of the prosthesis against and below the tissue or wall structure defining the defect.

Suture 22 is passed through the opposing conical members 14a, 14b, passing from the apex of one through the apex of the other. Suture 22 then is looped and returned back through the inner conical members 14a, 14b in the opposite direction. Looped suture 22 can be passed through the tubular structure 28 axially (or through the ends of the tubular structure 28, perpendicular to the axis thereof, as shown by dotted line 22') causing it to buckle, or collapse, when looped suture 22 is constricted during use. In the particular embodiment illustrated, both ends of looped suture 22 are passed through flat overlay sheet 26. Non-reversing knot 24 is tied in looped suture 22 and flat overlay sheet 26 is held in proximity to apex 18 of the upper one of the conical members 14a, 14b. The dead tail of the knot 24 is trimmed to length. The finished prosthesis is subjected to sterilization prior to use.

Figure 2:
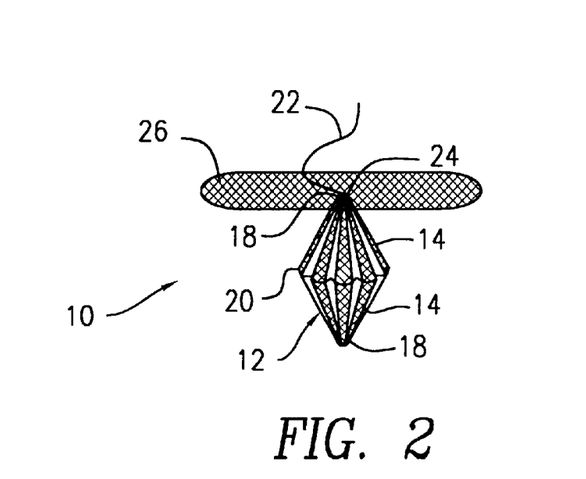
FIG. 2 is a perspective view of the assembled prosthesis depicted in FIG. 1.

The assembled prosthesis of FIG. 1 is illustrated in FIG. 2. Prosthesis 10 may be fabricated from any biocompatible medical woven, knitted or non-woven textile. In preferred embodiments, the prosthesis is fabricated from medical grade polypropylene mesh including knitted polypropylene monofilament mesh fabrics such as those available from Ethicon, Inc. under the Prolene trademark, as well as meshes available from Ethicon, Inc. under the Vicryl trademark. Other mesh materials useful in the invention include those available under the Marlex, Dacron, Teflon and Merselene trademarks. Alternatively, the desired effect of forcing tissue regeneration under the overlay patch can be accomplished through the selection of biocompatible absorbable materials for use in the fabrication of the expandable member. Examples of suitable materials are Vicryl and Panacryl sutures, available from Ethicon, Inc, and Polysorb suture, available from United States Surgical Corporation. Radially-expandable member 12 comprises conical members 14a, 14b fixedly attached one to the other proximate respective bases 20. Conical members 14a, 14b are configured to have an initial, non-expanded, major diameter that is substantially the same size or less than the diameter of the defect to be repaired. While the conical members 14a, 14b are (with the exception of flange 19) shown in the figure to be identical in structure, embodiments in which one is taller than the other are contemplated by the invention. The conical members 14a, 14b are positioned in opposition one to the other and bases 20 are aligned by flange 19. Once bases 20 are aligned, conical members 14a, 14b are fixedly attached to each other proximate the respective bases 20, e.g., in and around flange 19, as more fully described below. Bonding of the conical members 14a, 14b may be accomplished by stitching, gluing, welding or any other known form of attachment. Prosthesis 10 includes at least one flat sheet of mesh rolled into a tubular structure 28 (FIG. 1) and permanently located within cavity 30 (FIG. 1) formed by fixedly attached conical members 14a, 14b.

Tubular structure 28 may be fabricated from a flat sheet of polypropylene mesh that, once rolled into cylindrical shape, can been secured about its circumference with suture. Alternatively, tubular structure 28 may be formed by rolling a flat sheet of mesh into the cylindrical configuration and welding, stitching or otherwise bonding the rolled sheet at the ends. Tubular structure 28 (FIG. 1) is disposed inside cavity 30 (FIG. 1) formed by fixedly attached opposing conical members 14a, 14b and extends axially from the internal apex 18 of one to the internal apex 18 of the other. Tubular structure 28 aids in providing axial rigidity to the prosthesis when it is inserted into the defect.

Figure 3:
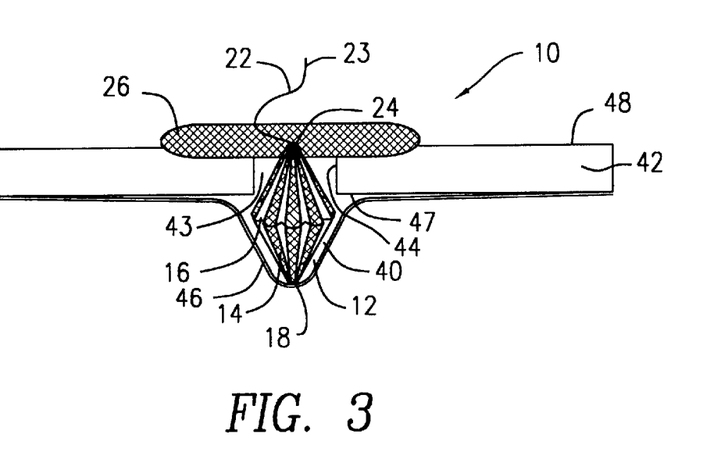
FIG. 3 is a schematic view of the prosthesis depicted in FIG. 2 when positioned within a defect in the fascia.
Figure 4:
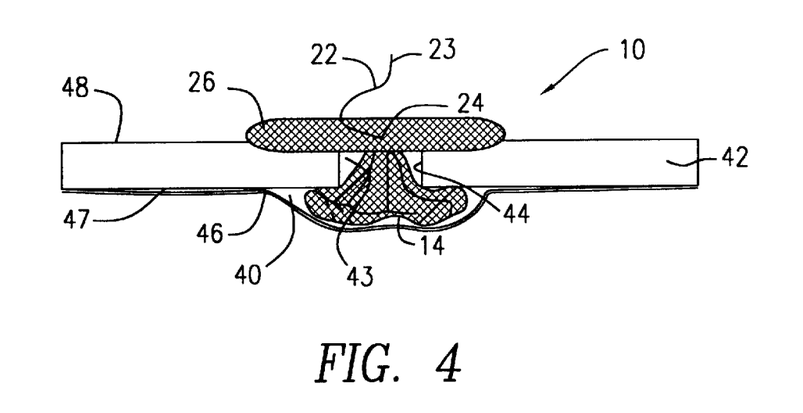
FIG. 4 is a schematic view of the prosthesis depicted in FIG. 3 after deployment, i.e. radial expansion, within the defect.

As shown in FIGS. 3 and 4, after hernia sac 40 has been dissected and/or ligated, prosthesis 10 is inserted into fascia defect 43. Once hernia sac 40 is free from walls 44 of defect 43 in fascia 42, hernia sac 40 is pressed back into the abdominal cavity. Apex 18 of the lower one of the conical members 14a, 14b is inserted into defect 43, causing peritoneum 46 to invert inwards into the abdominal cavity. Prosthesis 10 is inserted until overlay sheet 26 is flush with anterior side 48 of fascia 42. Free end 23 of suture 22 is pulled while prosthesis 10 is held in a forward position, i.e., flush with anterior side 48 of fascia 42. The tightening of suture 22 causes the opposing conical members 14a, 14b to be drawn together. The compression of the conical members 14a, 14b causes them to collapse axially onto themselves, thus causing the diameter of conical members 14a, 14b to expand radially and pleats 16 to open up or expand into a relatively flattened position, i.e., with a greater major diameter and a lesser axial length. This same action causes tubular structure 28, located within cavity 30, to buckle, collapse and expand radially outward. Knot 24 is pulled until it is fully tightened.

Free end 23 of suture 22 may be provided with a needle to enable attachment of the prosthesis 10 to the surrounding healthy tissue by sewing overlay sheet 26 into place. Alternatively, free end 23 of suture 22 can be trimmed off after final deployment and the overlay patch can be attached in place through the use of additional sutures, or may remain in a flattened condition in the anterior space.

The prosthesis 10 is able to accommodate the spermatic cord structures since it is pleated. When it is expanded, it relies only on the radial expansion force generated from the compression of the opposing textile conical members 14a, 14b to enlarge their diameters, as opposed to the use of additional semi-rigid rings or other rigid or semi-rigid members. Preferably, prostheses of the present invention do not comprise such rigid or semi-rigid devices. This ensures that the device is fully compliant to the natural anatomical structures.

The final configuration of expanded prosthesis 10, as seen in FIG. 4, both occludes fascia defect 43 on posterior side 47 and is expanded to fill the inner diameter of defect 43 in wall 44. The expansion of radially expandable member 12 on posterior side 47 of defect 43 prevents peritoneum 46 from entering defect 43. Additionally, this posterior expansion ensures that the repair is secure from re-herniation through the defect, since the conical mesh is forced into a relatively flat condition. As the scar tissue grows into the flattened conical layers, it is compressed further in the axial direction by scar tissue contraction. With the inclusion of overlay patch 26, located on anterior side 48 of defect 43, it is virtually impossible for the device to migrate either anteriorly or posteriorly.

Figure 5:
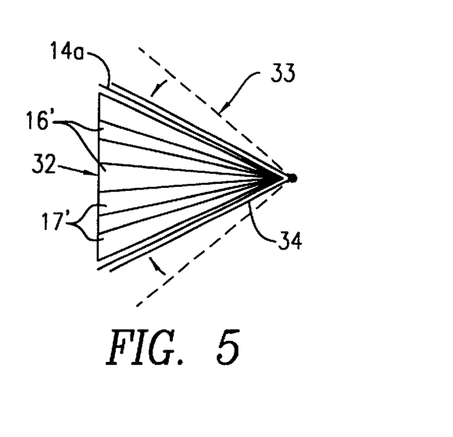
FIG. 5 is a schematic view of a die for making pleated conical elements of the prosthesis of FIGS. 1–4.

While radial expansion of the member may be effected by means for radially-expanding the member as discussed and depicted herein, prostheses that are self-expanding, i.e. self-collapsing, when placed in position within the fascia defect are included within the scope of the present invention. Such devices may be constructed such that they will deploy, i.e. collapse axially and radially-expand to occlude the defect, when positioned within a defect in response to conditions of the body surrounding the defect FIG. 5 shows a simplified diagram of an exemplary die system for forming the conical member 14a described above. The conical member 14a with longitudinal pleats 16 may be thermoformed from a generally flat disk of surgical mesh that has been placed over a male die element (mandrel) 32 having the same shape as the conical member 14a shown in FIGS. 1–4, i.e., a cone featuring a plurality of longitudinal valleys 16' (to form the pleats 16) and intervening land surfaces 17' (to form the lands 17 of the conical member 14a). After the surgical mesh (14a) has been placed over the outer surface of the male die element 32, a mating female die (clamp) element 33 is urged against the male die element 32 to press the surgical mesh (14a) into the surface features of the male die element, i.e., the longitudinal valleys 16' and intervening land surfaces 17', to impart the desired three dimensional shape to the mesh and to form the conical member 14a. The female die element 33 may be formed from a plurality of individual blade elements 34, preferably removably or hingedly attached to a common hub or pivot point and having an open configuration (shown in dotted lines) and which fold together to a closed configuration to press into the longitudinal valleys 16'. The conical member 14a clamped by blade elements 34 may then be heated to impose a set on the surgical mesh 14a such that it will retain the die shape after cooling and removal from the die set 32, 34. Any excess mesh 14a may then be trimmed off. As an alternative to the blade elements 34, the female die element 33 may have a continuous surface that is complementary to the surface of the male die element 32, or may have a plurality of individual extensions (not shown) elastically, rather than pivotally emanating from a common hub to form a cage structure for pressing the surgical mesh 14a into the longitudinal valleys 16' to form the longitudinal pleats 16 and to stretch the mesh 14a over the land surfaces 17' of the die 32.

Figure 6:
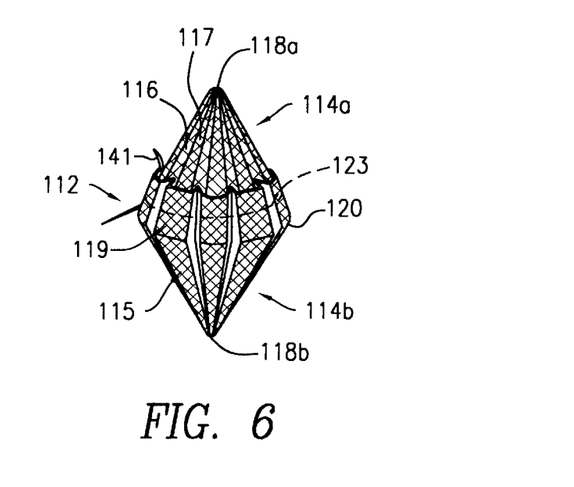
FIG. 6 is a perspective view of a prosthesis in accordance with a second embodiment of the present invention.
Figure 7:
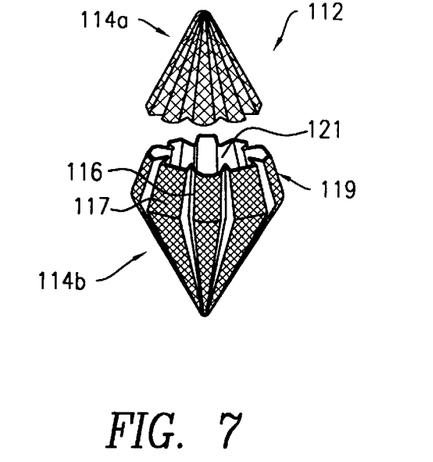
FIG. 7 is an exploded view of the prosthesis depicted in FIG. 5.

FIGS. 6 and 7 show an alternative radially expandable member 112 formed from conical members 114a and 114b. In contrast to the preceding expandable member 12, wherein two substantially identical conical members 14 were held in alignment and then secured together in opposition at the bases 20 of the cone shape, i.e., by gluing, stitching or welding at the flange 19, conical member 114a is attenuated such that it does not extend all the way to base line 120. As before, the conical members 114a, 114b are self aligning for the purpose of assembly. Conical member 114b has a conical portion 115 extending from the apex 118b to a base line 120. Base line 120 represents a redirection of the surgical mesh and a great diameter of the conical member 114b and the expandable member 112 as a whole. A flange portion 119 of the conical member 114b extends from the base line 120 and converges toward apex 118a, mimicking the shape of the conical portion 115 in reverse or mirror image. Conical member 114a has the same shape as conical portion 115 and matingly fits within the open end 121 defined by the flange portion 119, i.e., aligned by respective pleats 116 and lands 117. Conical member 114a overlaps flange portion 119 as shown by dotted line 123, providing an area for gluing or welding conical members 114a and 114b. The extent of conical members 114a and 114b can be varied to provide greater or lesser overlap. For example, conical member 114a could be identical to conical member 114b, providing a large area of overlap on either side of base line 120. Alternatively, conical member 114a can have a lesser extent than conical member 114b, as shown, such that there is a single layer of material present at the base line 120, which promotes bending at the baseline 120 and radial expansion of the expandable member 112.

Figure 8:
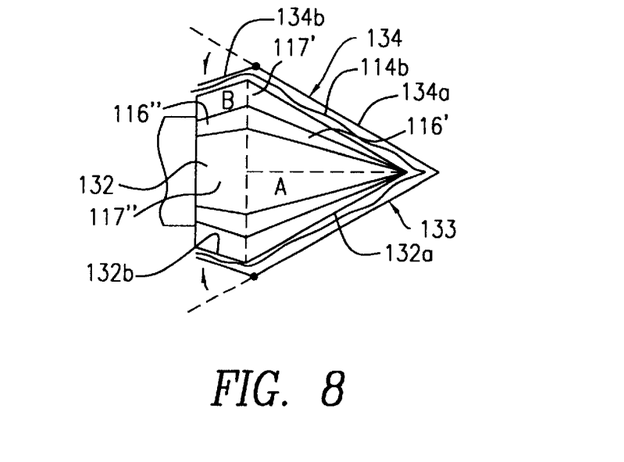
FIG. 8 is a schematic view of a die for making pleated conical elements of the prosthesis of FIGS. 6 and 7.

The manufacture of the radially expandable member 112 calls for the formation of the conical members 114a, 114b and their subsequent assemblage. FIG. 8 diagrammatically shows a die system that can be employed to form the conical member 114b, which includes a male die element 132 with conical portion 132a and conical flange portion 132b. A female die element 133 has a plurality of moveable blade elements 134, each having a conical portion 134a and a conical flange portion 134b for engaging the conical portion 132a and conical flange portion 132b, respectively, of the male die element 132. Either the conical portion 134a and/or the conical flange portion 134b of the blade element 134 is moveable from an open position (shown in dotted lines) to a closed position, either by virtue of hinges or by virtue of its being formed separately as a separate die element, i.e., the female die 133 may have a plurality of components. Alternatively, the female die element 133 may be in the form of a cage with multiple flexible fingers emanating from a common hub for pressing the mesh (114b) into the longitudinal valleys 116' of the conic portion 132a and the valleys 116" of the flange portion 132b.

Figures 9, 10, 11:
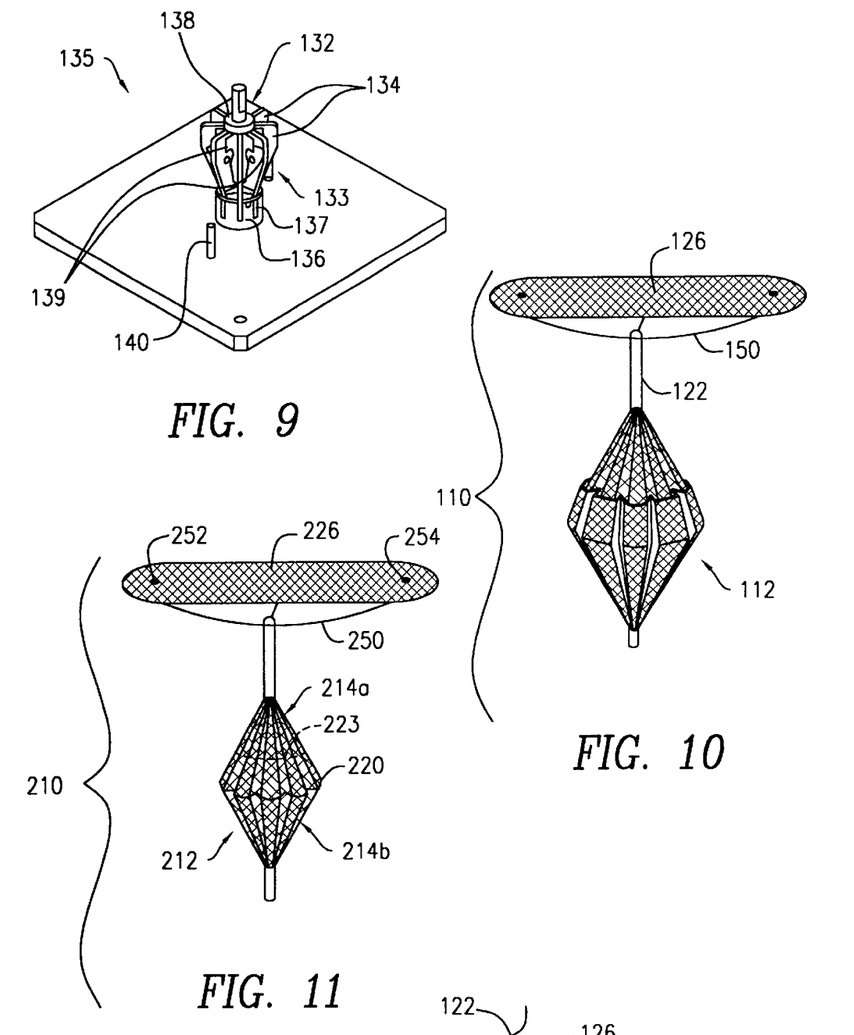
FIG. 9 is a perspective view of a forming station for forming a prosthesis in accordance with the present invention, e.g., as shown in FIGS. 6 and 7.
FIG. 10 is a perspective view of a prosthesis in accordance with a third embodiment of the present invention.
FIG. 11 is a perspective view of a prosthesis in accordance with a fourth embodiment of the present invention.

FIG. 9 shows a forming station 135 with a male die 132 (not visible) captured within the movable blade elements 134 of female die element 133. The blade elements 134 may be pivotally secured to the base 136 or, as shown, are removably retained in complementary shaped slots 137 and clamped in a closed position by flange 138. The blade elements 134 have a relief slot 139 for accommodating excess mesh material and/or a retention band for clamping the mesh on the male die 132. An orientation pin 140 may be utilized to position the mesh material in the forming station to achieve a selected orientation of the wales, warps, wefts, etc, promoting distortion-free forming of the material as the blade elements 134 are urged into position clamping the material against the male die 132. Optimal forming may require a particular sequential order of clamping the blade elements 134, depending upon the material, e.g., 114b used.

While the surgical mesh used to form the conical member 114a may be cut or otherwise formed in any selected two dimensional shape, a disk shape may be used to illustrate the relationship between the respective surface areas of the surgical mesh material 114b and the male die element 132. More specifically, for a male die element 132 having a conical portion 132a with a given altitude A and base B, the surface area thereof has two components, viz., that attributable to the surface area of the lands 117' and that attributable to the surface area of the longitudinal valleys 116'. Since the width of the valleys 116' of the die 132 directly decreases the land 117' area of the die 132, the total surface area may be controlled by varying the depth and shape of the longitudinal valleys 116', which can be selected to "use" a desired amount of the surface area of the surgical mesh 114b. Similarly, the longitudinal valleys 116" in the conical flange portion 132b of the male die element 132 may have a selected depth, shape etc. such that the surface area of the flange portion 132b may be altered by varying these dimensions. The valley 116' dimensions for the conical portion 132a may be different than the valley 116" dimensions of the conical flange portion 132b. Alternatively, the valley 116', 116" dimensions may be consistent and symmetrical.

The foregoing observations concerning the surface areas of the conical portion 132a and conical flange portion 132b are noteworthy in that a given disk-shaped sample of surgical mesh has a surface area that increases radially in accordance with the relationship ($\pi r^2$). The surface of a cone increases from the apex 118 to the base 120 in accordance with the relationship $\pi rs$; where $s=(r^2+b^2)^{1/2}$. As a consequence, the area of the material disk increases along its radius, as does the area of the conic portion 132a from the apex to the base. Any mismatch of surface areas must be accounted for by stretching the mesh. The flange portion 132b of the male die element 132 exhibits a departure from the surface area of the material disk, in that while the converging flange portion 132b of the die 132 increases the total surface area, it does so at a decreasing rate (due to its convergence) at the same time that surface area of the mesh 114b increases by the square of the radius. Accordingly, after the surgical mesh material extends beyond the great diameter of the male die 132 (at base B) and starts to cover the converging conical flange portion 132b of the die 132, an excess of mesh material must be accounted for in order to bring the mesh into conformance with the die 132 shape.

In accordance with a first approach, the die 132 is formed with a valley 116" number (frequency) and depth (magnitude) such that the surface area of the mesh material 114b matches that of the flange 132b but is less than that required to cover the surface area of the conical portion 132a (including the surface area of the valleys 116') proximate to the great diameter at base B without stretching. In accordance with this method, the surgical mesh material 114b is wrapped over the male die element 132 covering both the conical portion 132a and the conical flange portion 132b of the die 132. The female die element 133 is then clamped over the male die element 132 forcing the mesh material 114b into the valleys 116', 116" provided in the male die element 132. Because the surface area of the material 114b is less than that of the die 132, the material 114b will be stretched thinner in the areas where the surface areas of the material 114b and the die 132 do not match. This results in the mesh 114b being thinner and more porous in those areas where it is stretched, primarily in the area of the great diameter proximate base B. This thinning in the area of the base B of the conical portion 132a enhances the hinge effect present at baseline 120 of the expandable member 112, promoting the expansion of the expandable member 112.

Once the mesh has been conformed to the surfaces of the complementary die elements 132, 133, the mesh is heated, e.g., by convection, radiation and/or conduction through the die elements 132, 133. Heating relieves the stress in the highly oriented, drawn fibers of the surgical mesh 114b allowing the mesh to permanently set in the shape imposed upon it by the dies 132, 133. The female die 133 can then be removed and the mesh cooled prior to removal from the male die 132. In using the foregoing technique, the mesh 114b must be securely held against the male die element 132 to prevent it from creeping along the surface of die 132 prior to its being clamped tightly by the female die element 133. The same process may be undertaken to form conical member 114a. If the extent of 114a is chosen such that no flange 119 is present (as shown in FIG. 7) the foregoing considerations concerning matching the respective surface areas of the mesh 114a and the male die 132 are simplified.

An alternative approach for forming conical member 114b is to use a male die 132 with a surface area less than that of the surgical mesh 114b, in particular, in the area of the flange portion 132b of the die 132. The mesh 114b is clamped to the male die element 132 such that there is an excess of mesh material 114b distributed in the valleys 116', 116" of the die 132. The mesh 114b is then heated by convection to an elevated temperature, causing the fibers of the mesh 114b to stress relieve and to shrink. The shrinkage of the mesh 114b causes the surface area of the mesh to be reduced through a localized reduction in porosity in the conical flange portion 119. This method does not involve the same forces that induce the slippage of mesh on the face of the male die 132 and eliminates the excess mesh material that might otherwise result in irregularities in the finished conical element 114b, such as everted pleats.

As can be appreciated from FIGS. 6 and 7, the finished conical elements 114a and 114b nest together in natural alignment due to the alignment of the pleats 116 and lands 117. Having thus been aligned, the overlap between 114a and 114b can be joined by a variety of conventional means including adhesives or welding. One advantageous method includes utilizing a plurality of metal pins 141 (see FIG. 6) to form a backing cage for the overlap area of 114a and 114b during exposure to ultrasonic welding. While only one pin 141 is shown, it should be appreciated that a series of pins 141 would be used to provide multiple ultrasonic welds around the circumference of the expandable element 112.

As yet another approach to forming the expandible element 112, internal stiffening ribs can be formed within the pleats 116 through the controlled application of heat and clamping the mesh in the dies 132, 133, viz., by differential shrinkage of the mesh to form stiffening ribs. More specifically, a mesh disk is provided having a greater surface area than that of the male die 132, i.e., if the mesh 114b were pressed against the surface of the male die 132 (including the lands 117', 117" and valleys 116', 116") there would be excess mesh 114b, particularly in the flange area 132b of the die 132. The mesh 114b is applied over a cold male die element 132. A female die 133 having independently moveable blade elements 134 for abutting against the land areas 117'. 117" of the male die 132 and independently moveable portions for abutting against the valleys 116', 116" in the male die 132 is applied over the mesh 114b to clamp the land areas 117 only. This leaves the pleats 116 free to assume any position relative to the valley areas 116', 116" of the male die 132. In practice, the unclamped pleats 116 tend to bulge out from the surface of the male die 132. The unclamped pleats 116 are subject to heating to a point that the exposed mesh undergoes shrinkage. The die itself is cool and the lands 117 of the mesh that are clamped in the die are shielded from heating. The heating may be done by convection, radiation (heat lamp) or other conventional methods. While the mesh 114b is still hot, the moveable portions of the female die 133 that correspond to the pleats 116, i.e., that insert into the valleys 116', 116" of the male die 132, are applied to the mesh 114b to clamp the exposed hot pleats 116 into the valleys 116', 116" of the male die 132. The female die 133 is dimensioned relative to the male die 132 to produce a selected thickness for the mesh material in each area, i.e., in the land areas 117 and the pleat areas 116. The heat source is removed and the mesh 114b is allowed to cool while clamped in the die to retain its set shape. Because the pleats 116 were exposed to heating and experienced shrinkage, the density of the pleats 116 is greater (lower porosity) than the lands 117. When conical elements 114a, 114b formed in this manner are mounted together in opposition, as explained above, the high density regions of the mesh, i.e., the pleats 116, act as stiffening ribs. When the radially expandable member 112 is axially collapsed, the higher density and more rigid pleats 116 resist bending and force the lands 117 apart to deploy the radially expandable member 112. The same concept for forming stiffened, higher density regions in the conical members 114a, 114b described above can be generally applied to surgical mesh to form mesh products with selected stiffened regions. More particularly, by clamping certain regions of the mesh in a cold die with other slack portions subject to heating and shrinkage, zones of higher density/greater rigidity of any devised shape or distribution can be formed.

Referring to FIG. 10, prosthesis 110 includes overlay patch 126 slidably attached to radially-expandable member 112. As shown, filament 150 is passed through looped suture 122 and affixed at its terminal ends to overlay patch 126. When radially expandable member 112 is placed in the defect, overlay patch 126 may be maneuvered to one side to effect attachment to fascia 142.

FIG. 11 shows a prosthesis 210 having an overlay patch 226 slidably attached to a radially expandable member 212 by an elongated filament 250. The radially expandable element 212 has conical portion 214b with a flange (shown by dotted line 223) that is covered by conical portion 214a, which extends to baseline 220. As in the previous embodiment, the filament 250 is joined to the overlay patch 226 at two spaced points 252, 254, e.g., by tying, plastic welding or by being restrained from pulling through the overlay patch 226 material by knots or enlarged ends that exceed the size of the material of the pores of the overlay patch 226. Intermediate the points of connection 252, 254, the filament 250 extends substantially parallel to the overlay patch 226. While a single filament 250 is shown, a plurality of parallel filaments 250 may be utilized. The radially expandable member 212 is moveable along the filament(s) 250 defining a motion "track" relative to the overlay patch 226.

Figure 12:
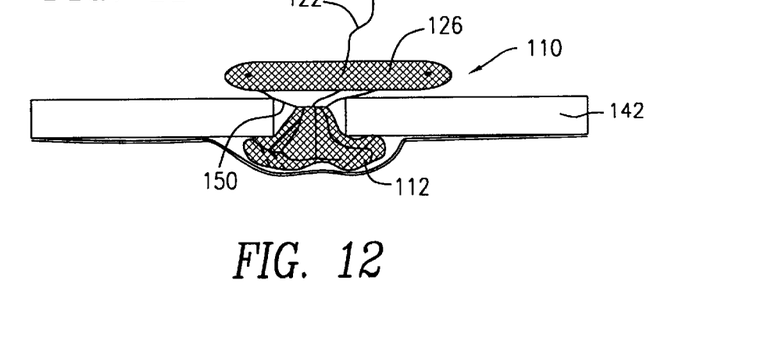
FIG. 12 is a schematic view of the prosthesis of FIG. 11 within a fascia defect.

Because the expandable member 212 is slidable on the filament 250, the expandable member 212 may be positioned relative to the overlay patch 226 to maximally conform to the anatomy of the patient and the surgical repair encountered, as shown in FIG. 12. More particularly, the expandable member 212 may be inserted into the facia void and then the position of the overlay patch 226 may be adjusted to coincide with the position of maximally effective surgical attachment, viz., to be amenable to attaching the overlay patch 226 to healthy tissue, to bridge over weak, unhealthy tissue, and also to conform to the patients' local anatomical shape. The overlay patch 226 may have any desired shape, such as a keyhole, oval, circular or rectangular shape.

It will be understood that the embodiments described herein are merely exemplary and that a person skilled in the art may make many variations and modifications without departing from the spirit and scope of the invention. All such variations and modifications are intended to be included within the scope of the invention as defined in the appended claims.

We claim:

1. A hernia repair prosthesis, comprising:
an occlusive member for aiding in the occlusion of a defect in facia tissue, said occlusive member being convertible from a first configuration with a first axial length and first major radial extent to a second configuration with a second axial length and a second major radial extent, said second axial length being less than said first axial length and said second major radial extent being larger than said first major radial extent, said occlusive member having a pair of subsections each having an apex and each flaring outwardly therefrom towards a terminal end, said apexes being disposed at opposite ends of said occlusive member with said terminal ends overlapping, said pair of subsections fixedly attached proximate said overlapping terminal ends in said first configuration and said second configuration.

2. A hernia repair prosthesis, comprising:

an occlusive member for aiding in the occlusion of a defect in facia tissue, said occlusive member being convertible from a first configuration with a first axial length and first major radial extent to a second configuration with a second axial length and a second major radial extent, said second axial length being less than said first axial length and said second major radial extent being larger than said first major radial extent, said occlusive member having a pair of subsections each having an apex and each flaring outwardly therefrom towards a terminal end, said apexes being disposed at opposite ends of said occlusive member with said terminal ends overlapping, said pair of subsections conjoined proximate said overlapping terminal ends, a first of said pair of subsections having an inwardly converging flange disposed at said terminal end thereof.

3. The prosthesis of claim 2, wherein said pair of subsections are pleated, generally cone-shaped members with a plurality of pleats and a plurality of lands therebetween, said flange of said first subsection extending from a geometric base of said first subsection in a direction generally parallel to the surface of said second subsection and extending toward the apex of said second subsection.

4. The prosthesis of claim 3, wherein said occlusive member is generally radially symmetric.

5. The prosthesis of claim 4, wherein said geometric base of said first subsection is the approximate geometric base of said second subsection and said occlusive member is generally symmetric about a plane passing through said geometric base of said first subsection.

6. The prosthesis of claim 3, wherein each of said lands and pleats of said first subsection and said lands and pleats of said second subsection align and nest relative to each other at said overlapping terminal ends.

7. The prosthesis of claim 6, wherein said flange of said first subsection overlays said second subsection.

8. The prosthesis of claim 6, wherein said second subsection overlays said flange of said first subsection.

9. The prosthesis of claim 3, wherein said occlusive member is formed from a surgical fabric.

10. The prosthesis of claim 9, wherein said fabric is less dense at said geometric base than said fabric not at said geometric base.

11. The prosthesis of claim 9, wherein at least a portion of said fabric of said flange is more dense than said fabric not of said flange.

12. The prosthesis of claim 9, wherein at least a portion of said fabric forming said pleats is more dense than said fabric forming said lands.

13. The prosthesis of claim 3, further including a suture loop extending between said apexes of said first and second subsections, said loop being reducible in size to convert said occlusive member from said first configuration to said second configuration.

14. The prosthesis of claim 13, further including an overlay sheet surgically attachable to a first side of the fascia tissue, said overlay sheet being attached to said occlusive member.

15. The prosthesis of claim 14, wherein said overlay sheet is attached to said occlusive member via a filament extending from a first point of attachment to said overlay sheet to a second point of attachment, said filament extending substantially parallel to said overlay sheet between said first and second points of attachment, said occlusive member slidably attached to said filament to permit said occlusive member to assume a selected position relative to said overlay sheet between said first and second points of attachment.

* * * * *